United States Patent
Moody et al.

(10) Patent No.: US 7,341,059 B2
(45) Date of Patent: Mar. 11, 2008

(54) BREATHING ASSISTANCE APPARATUS

(75) Inventors: Paul Moody, Auckland (NZ); Bronwyn Nicola Cotter, Auckland (NZ); Neil Prime, Auckland (NZ); Glenn Whyte, Auckland (NZ); Matthew Jon Payton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 406 days.

(21) Appl. No.: 11/106,252

(22) Filed: Apr. 14, 2005

(65) Prior Publication Data

US 2005/0178386 A1     Aug. 18, 2005

Related U.S. Application Data

(62) Division of application No. 10/357,753, filed on Feb. 4, 2003.

(30) Foreign Application Priority Data

Feb. 4, 2002   (NZ) ..................................... 517030
Apr. 10, 2002  (NZ) ..................................... 518289

(51) Int. Cl.
    *A62B 9/02*    (2006.01)
    *A61M 16/00*   (2006.01)

(52) U.S. Cl. ........................... 128/205.24; 128/204.18; 128/204.23

(58) Field of Classification Search ........... 128/204.18, 128/204.23, 204.25, 204.26, 201.28, 204.27, 128/205.13, 205.24, 205.14–205.19, 207.14–207.16, 128/202.28, 202.29, 203.11, 207.12, 204.28
See application file for complete search history.

(56) References Cited

U.S. PATENT DOCUMENTS

| | | | |
|---|---|---|---|
| 1,162,416 A | 11/1915 | Teter | |
| 1,632,449 A | 6/1927 | McKesson | |
| 3,799,185 A | 3/1974 | Milnes et al. | |
| 4,655,213 A | 4/1987 | Rapoport et al. | |
| 5,207,220 A | 5/1993 | Long | |
| 5,746,199 A * | 5/1998 | Bayron et al. | 128/205.24 |
| 5,762,063 A | 6/1998 | Coates et al. | |
| 5,839,436 A | 11/1998 | Fangrow, Jr. et al. | |
| 6,006,748 A | 12/1999 | Hollis | |
| 6,041,775 A * | 3/2000 | Century | 128/200.14 |
| 6,058,933 A | 5/2000 | Good et al. | |
| 6,067,984 A * | 5/2000 | Piper | 128/205.24 |
| 6,086,529 A * | 7/2000 | Arndt | 600/114 |
| 6,202,645 B1 * | 3/2001 | Brown | 128/205.24 |
| 6,629,530 B2 * | 10/2003 | Cise | 128/205.24 |
| 6,886,561 B2 * | 5/2005 | Bayron et al. | 128/205.24 |
| 7,207,332 B1 * | 4/2007 | Lugtigheid | 128/204.28 |

FOREIGN PATENT DOCUMENTS

| | | |
|---|---|---|
| FR | 1580403 | 9/1969 |
| FR | 2709066 | 2/1995 |
| GB | 2222778 | 3/1990 |
| WO | WO 00/22985 | 4/2000 |

\* cited by examiner

*Primary Examiner*—Teena Mitchell
(74) *Attorney, Agent, or Firm*—Trexler, Bushnell, Giangiorgi, Blackstone & Marr, Ltd.

(57) ABSTRACT

A connector for resuscitating an infant or neonate is disclosed. The pressure is varied between Peak Inspiratory Pressure (PIP) and Peak End Expiratory Pressure (PEEP) by the occlusion of the PEEP outlet. The PEEP outlet may either allow variable PEEP, by adjustment, or substantially flow independent fixed PEEP using a novel umbrella valve. A duck billed valve is included for suctioning of surfactant delivery during resuscitation. The connector is adapted to one handed use.

7 Claims, 9 Drawing Sheets

BREATHING ASSISTANCE APPARATUS

This application is a divisional co-pending application Ser. No. 10/357,753, filed on Feb. 4, 2003 and entitled "Breathing Assistance Apparatus".

FIELD OF INVENTION

The present invention relates to the use of a pressure regulator in conjunction with a breathing assistance apparatus, particularly though not solely, for regulating the pressure of gases supplied to a patient from a Positive End Expiratory Pressure (PEEP) apparatus or for an infant resuscitation device.

BACKGROUND

At the moment of their first breath, a baby's lungs are collapsed and filled with fluid. The pressures needed to open such lungs, and keep them open, are several times that of a normal breath until the fluid is displaced and the lungs have filled with air. To generate these large pressures, the baby must have strong respiratory muscles, as well as a chemical called surfactant in their alveoli. Surfactant reduces the surface tension of the fluid within the alveoli, preventing the alveolar walls from sticking to each other, like coasters to coffee cups when there is water between them.

Neonates have difficulty in opening their lungs and keeping them open. Reasons for this include:

a) Weak respiratory muscles and low surfactant levels. This means that they cannot generate enough pressure to open the lungs and, should they be resuscitated, tire quickly with the effort of keeping open alveoli lacking in surfactant.

b) Underdeveloped internal tissue structure to support the alveoli.

c) Slower clearance of lung fluid. In very premature neonates, fluid may continue to be secreted in the alveoli even after birth d) A soft chest wall, horizontal ribs, and a flatter diaphragm contribute to reduce the inspiratory capacity.

e) The mixing of oxygenated and deoxygenated blood raises blood pressure in the lungs, increasing fluid movement from the blood vessels into the lung tissue. The reduced blood oxygen level starves tissue of oxygen and further weakens respiratory muscles.

f) Weak neck muscles and a lack of neck fat reduce upper airway stability so that collapse on inspiration may occur.

g) Collapsed, damaged alveoli secrete proteins that reduce surfactant function.

To alleviate this it is known to apply Positive End Expiratory Pressure (PEEP) during respiration, resuscitation or assisted respiration (ventilation). In applying PEEP, the neonate's upper airway and lungs are held open during expiration against a pressure that stops alveolar collapse. Lung fluid is pushed back into the circulating blood, alveolar surfactant is conserved, and a larger area of the lung participates in gas exchange with the blood. As blood oxygenation and carbon dioxide removal improves, more oxygen is delivered to growing tissues, while less oxygen and energy is consumed by respiratory muscles. In the case of resuscitation or ventilation the pressure is varied between a Peak Ispiratory Pressure (PIP) and the PEEP value until the patient/infant is breathing spontaneously.

In order to provide the PEEP across a range of flow rates, some method is required to regulate the pressure. It is known in the art to provide a valve near the infant, which actuates at a level of pressure (i.e.: the PEEP value) to allow the gases to vent externally. Such valves may employ a spring-loaded valve, which in turn requires the use of high quality springs, which have been individually tested to give a high tolerance spring constant in order to ensure that it actuates at a value substantially that of the maximum safe pressure. Both the manufacture and testing of such a spring necessitates that its cost will be correspondingly high. Accordingly it would be advantageous to provide a pressure relief valve for a breathing assistance system which did not involve the use of such a high tolerance spring.

Figure 4A:
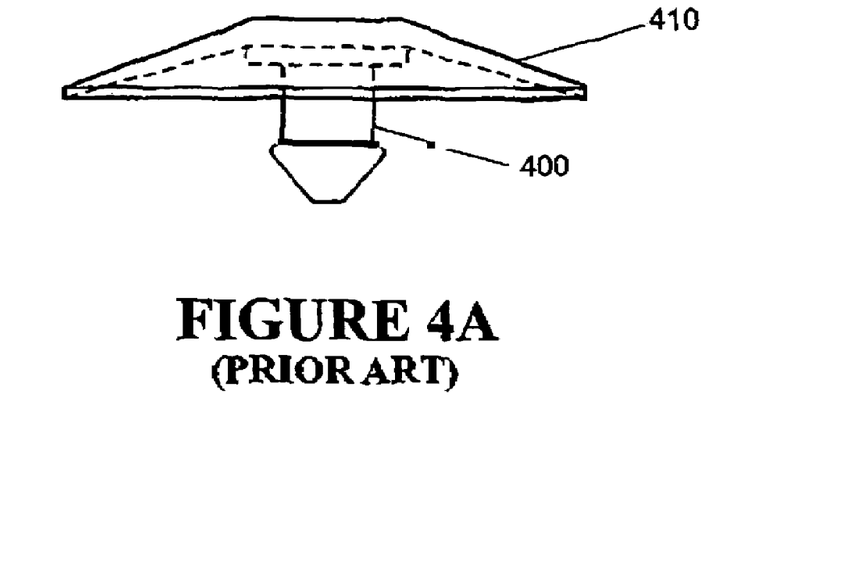
FIG. 4a is a cross-section of a prior art umbrella valve
Figure 4B:
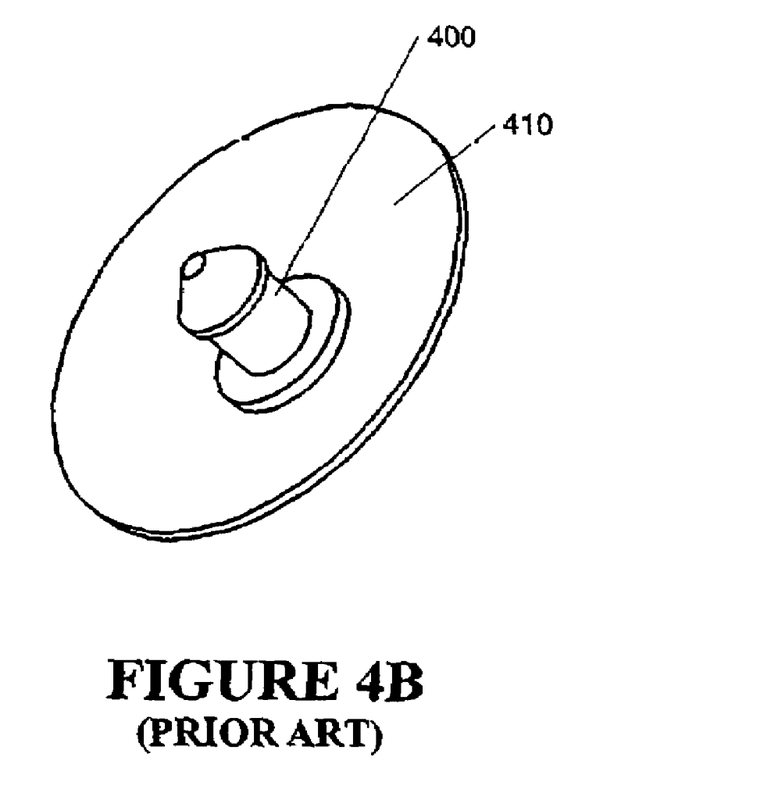
FIG. 4b is a perspective view of a prior art umbrella valve
Figure 5:
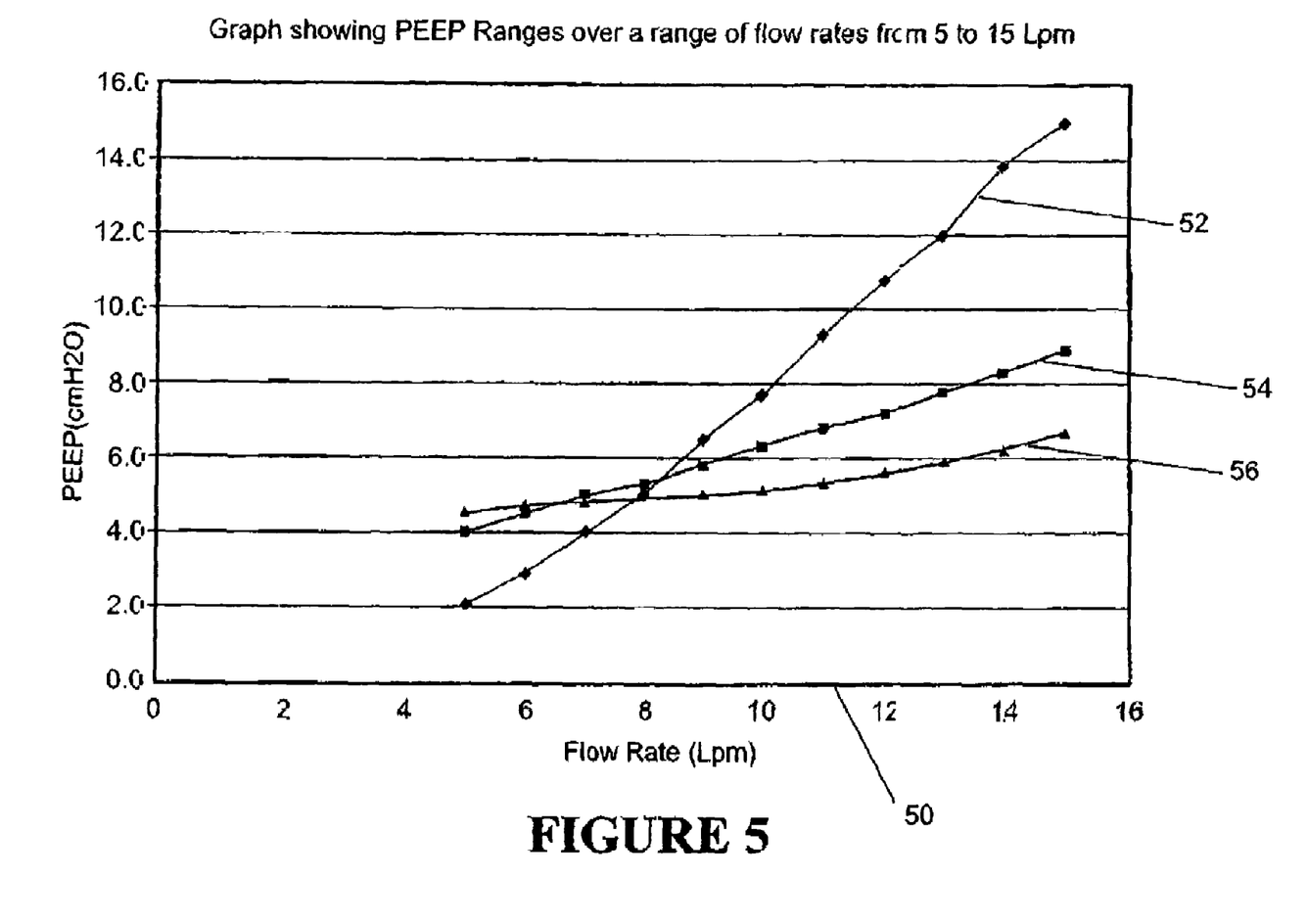
FIG. 5 is a graph comparing pressure ranges of different valves over a flow range of 5-15 liters/minute.

Also such valves are known to have substantial variation of the relief pressure with flow rate. For example as seen in FIG. 5 the delivered pressure is shown for a range of valves. Over a given range of flow rates 50 a variable orifice 52 gives a wide range of delivered pressure. An improvement on this is a prior art umbrella valve (for example the "umbrella check valve" manufactured by Vernay Laboratories Inc. shown in FIGS. 4a & 4b) which delivers a lower variation 54 in delivered pressure. However in all cases the variation in delivered pressure of prior art valves would desirably be reduced for this application.

SUMMARY OF INVENTION

It is an object of the present invention to provide a pressure regulator which goes some way to achieving the above-mentioned desiderata or which will at least provide the Healthcare industry with a useful choice.

Accordingly, in a first aspect, the present invention consists in a device for use with a breathing assistance apparatus which in use conveys gases to a neonatal infant requiring resuscitation or breathing assistance, comprising:

a housing, having an inlet and a first outlet, said inlet adapted to be in fluid communication with a breathing assistance apparatus and said first outlet adapted to be in fluid communication with said infant, said housing also including an aperture adapted to allow a surfactant delivery tube to be introduced and removed through said aperture, said device adapted to that said delivery tube can deliver surfactant to a patient while said breathing assistance apparatus provides resuscitation breathing assistance, said aperture including a seal adapted to prevent gas flow through said aperture in use, said housing further including a second outlet that is adapted to act as a venting aperture, and a pressure relief valve located in the flow path between said inlet and said second outlet, said second outlet and said housing mutually adapted so that in use a user can hold said housing in position with one hand, and occlude and un-occlude said second outlet with one finger of said one hand to vary the pressure at said first outlet between PIP with said second outlet occluded and all the flow of gases from said inlet passing through said first outlet, and PEEP with said second outlet unoccluded, and a portion of said flow of gases from said inlet passing through said second outlet.

Preferably said pressure relief valve comprises an elastomeric member having at least two configurations: a first configuration where said elastomeric member blocks the flow path between said inlet and said second outlet, and a second configuration where said elastomeric member allows a portion of the flow of gases from said inlet to flow through second outlet, said elastomeric member adapted to switch from said first configuration to said configuration at a predetermined low rate.

Preferably said seal is formed as a duck billed valve, opening into said housing.

Preferably said aperture and said first outlet are arranged substantially coaxially.

Preferably, said pressure relief valve comprises a screw-on cap located over said second outlet, and housing including a thread to allow location and adjustment of said screw-on cap, and wherein said second outlet is formed as a jet outlet, the flow rate of the gases through said jet outlet varied by adjusting the position of said cap by rotating said cap on said thread, and wherein the closer the screw-on cap is to said jet outlet, the smaller the gas flow rate through said jet outlet.

Preferably, said seal is formed as a duck billed valve, opening into said housing.

Preferably, said aperture and said first outlet are arranged substantially coaxially.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention includes a connector for resuscitating an infant or neonate. The delivered pressure is varied between Peak Inspiratory Pressure (PIP) and Peak End Expiratory Pressure (PEEP) by the occlusion of the PEEP outlet. The PEEP outlet may either allow variable PEEP, by adjustment, or substantially flow independent fixed PEEP using a novel umbrella valve. A duck billed valve is included for suctioning of surfactant delivery during resuscitation. The connector is adapted to one handed use. The fixed PEEP valve avoids the need for adjustment as flow changes and provides more effective therapy.

Figure 1:
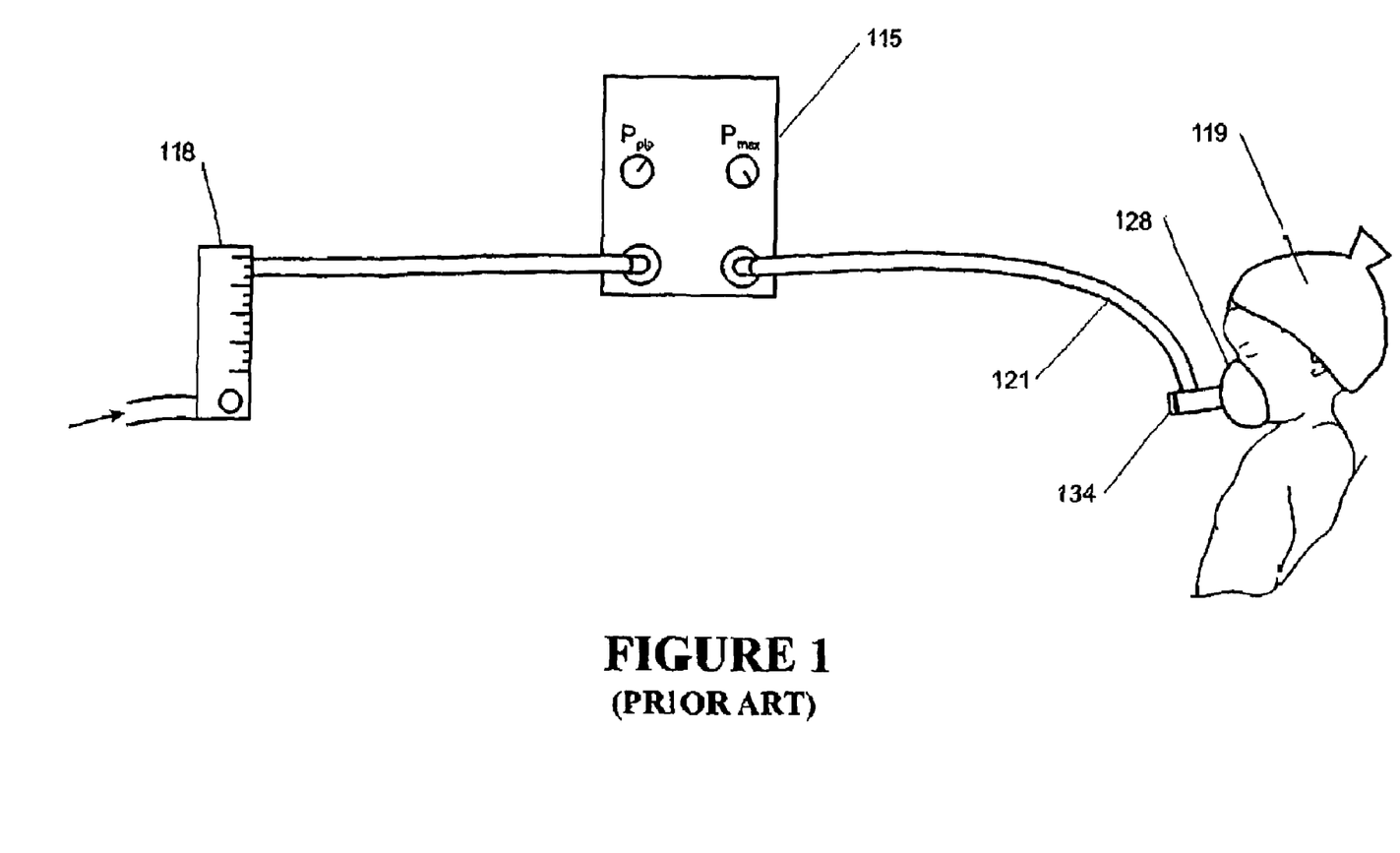
FIG. 1 is a block diagram showing a typical configuration for supplying breathing assistance to a neonate in accordance with the prior art.

Referring now to FIG. 1 in which a typical application is depicted. A Positive End Expiratory Pressure (PEEP) system is shown in which an infant 119 is receiving pressurized gases through a nasal mask 128 (or endotracheal tube or other interface as are shown in the art) connected to an inhalatory conduit 121, preferably for resuscitation. Either the mask 128 or the inhalatory conduit 121 can include the pressure regulator 134 to control the pressure of gas delivered to the infant. The inhalatory conduit 121 is connected to the outlet of a resuscitator apparatus 115, which is in turn connected to a flow regulator and air supply 118 (which provides gas to the resuscitator at 50 psi or thereabouts).

It should be understood that the present invention, however, is not limited to resuscitation, or the delivery of PEEP gases but is also applicable to other types of gas delivery systems.

Pressure Regulator

Figure 2A:
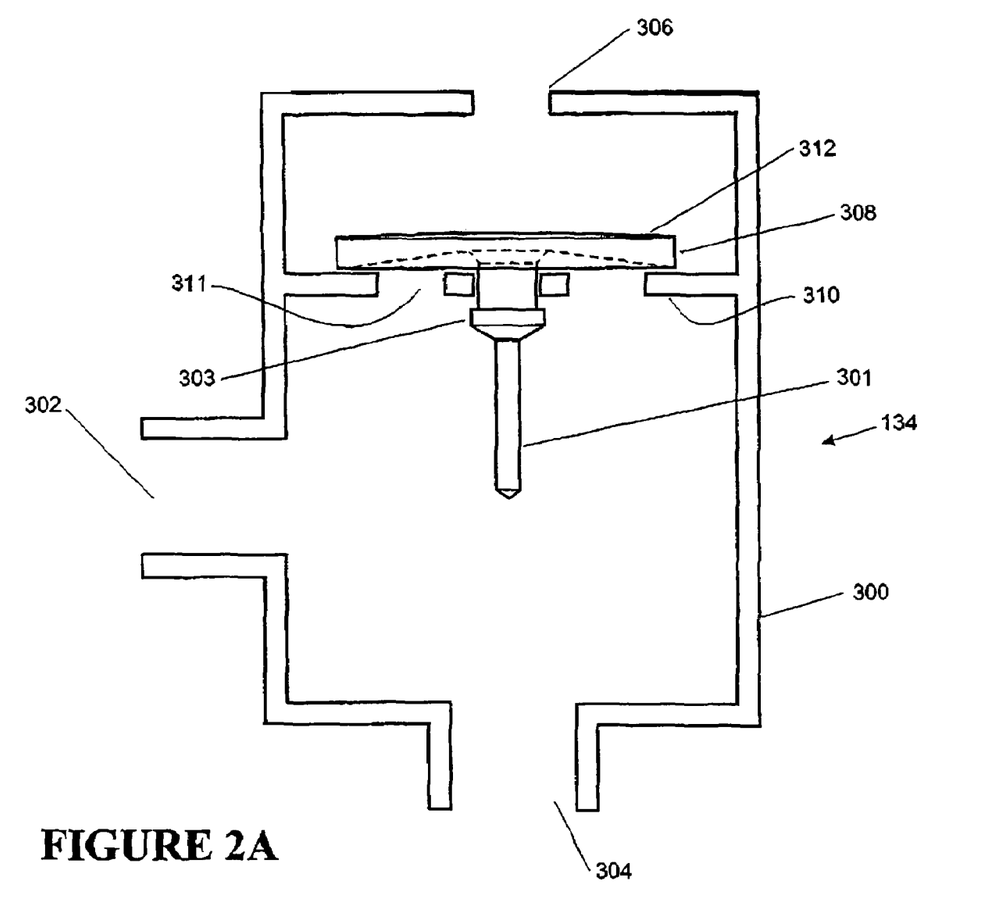
FIG. 2a is a sectional view of the pressure regulator according to the preferred embodiment of the present invention.
Figure 2B:
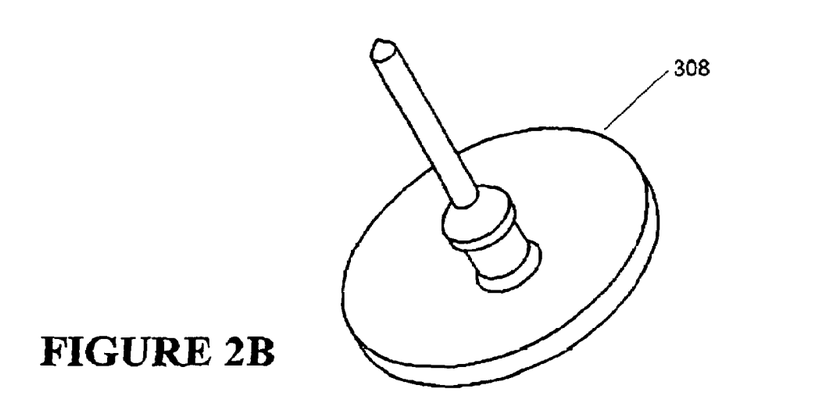
FIG. 2b is a perspective view of the valve member according to the preferred embodiment of the present invention.
Figure 3:
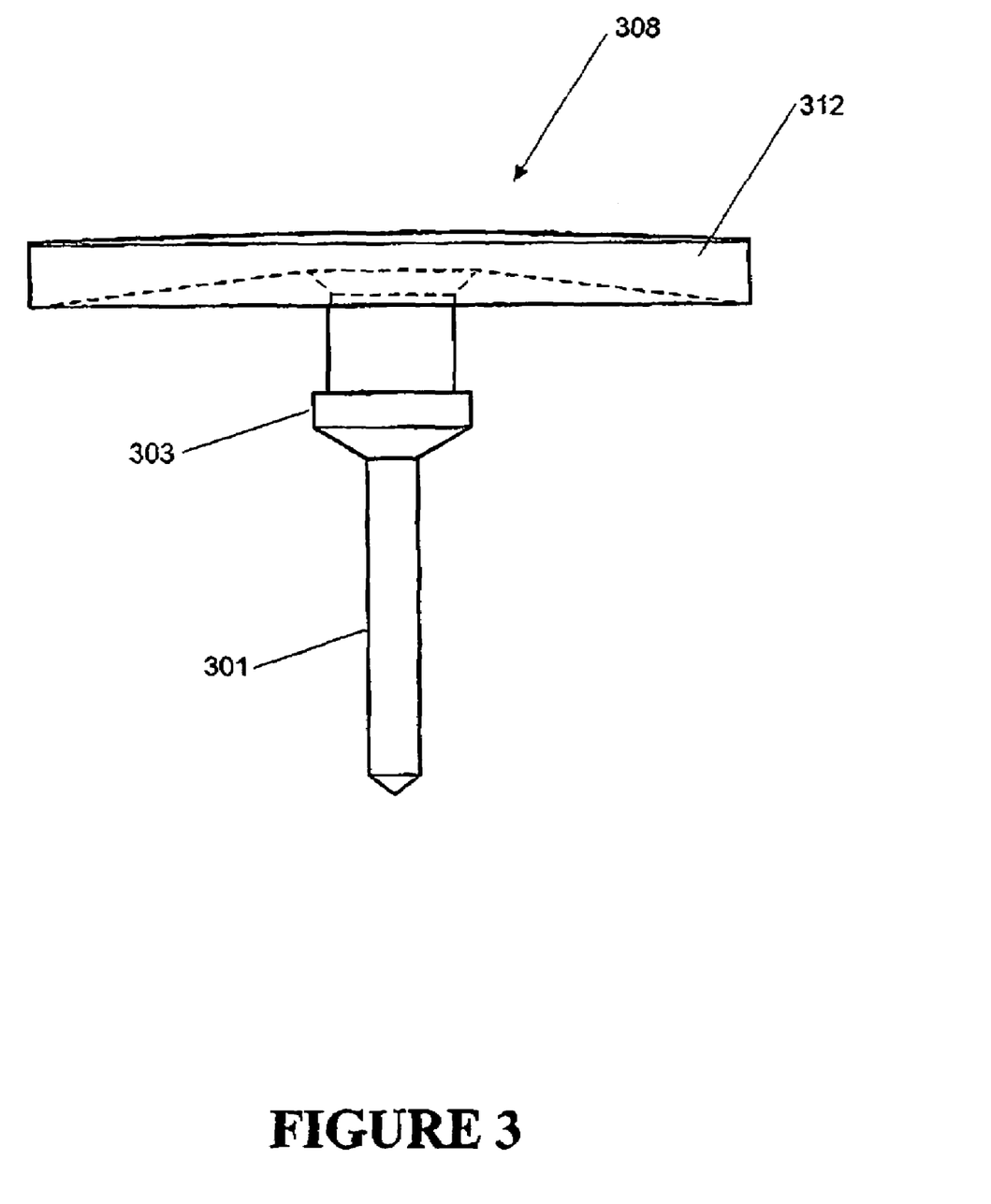
FIG. 3 is a dimensioned side view showing hidden detail of the valve member according to the preferred embodiment of the present invention.

In the preferred embodiment of the present invention the pressure regulator 134, is shown in FIGS. 2 and 3 in detail. In the preferred embodiment the regulator 134 is disposed within the mask 128 although it will be appreciated that it can be allocated in a separate assembly, so long as it is proximate the infant.

Referring particularly to FIG. 2a we see the preferred embodiment of the pressure regulator 134. The pressure regulator 134 includes a housing or manifold 300 with an inlet 302 and two outlets. A first outlet 304 supplies the respiratory gases to the infant. A second outlet 306 is an external orifice as described previously to vary pressure between the PIP and PEEP. Located between the inlet 302 and the orifice 306 is the PEEP valve 308 according to the present invention.

The PIP is adjusted at the resuscitator 115 to a desired level. The delivered gases are varied between the PIP with orifice 306 near the infant occluded, and the PEEP with the orifice 306 unoccluded. In this fashion resuscitation of an infant can be attempted by varying between the PIP and PEEP at the normal rate of breathing.

The purpose of the PEEP valve 308 according to the preferred embodiment of the present invention is to keep the Positive End Expiratory Pressure (PEEP) at a reasonably constant level independent of changes in flow rate.

Desirably for infant respiratory assistance the PEEP value should be approximately 5 cmH$_2$O, independent of the flow rate. Preferably the interface needs to be simple and cost effective, as it is a single-use product. Also, due to the nature of this application, a valve with many small separate parts, such as a spring valve, is not a viable option.

The present invention includes a small umbrella valve 308 made of an elastomeric material, positioned on a valve seat 310 seen particularly in FIGS. 2a & 2b. Valve seat 310 defines an internal venting aperture 311 which is covered by the valve 307 in a closed position. Preferably this valve is included as part of the nasal mask or endotracheal tube. As the flow rate increases, the umbrella valve flaps 312 lift up thereby letting more air out underneath and therefore keeping the pressure inside the manifold 300 at a constant level.

The umbrella valve according to the present invention differs from other prior art umbrella valves in the material and dimensions, the material being Silastic liquid silicone rubber Q7-4840. The proportions of the umbrella valve can be seen in FIG. 3. In articular comparing FIG. 3 to FIG. 4A we see the present invention has a characteristic flap 312 which is thicker at its periphery than at its center. The valve 308 includes a shaft 301 having a retaining flange 303.

Due to the design used, the present invention umbrella valve does not act as a 'pop-off' valve like most umbrella valves as it is not designed to open at a specific predetermined pressure. Most umbrella valves are designed to open at a specific 'cracking pressure', such as that shown in FIGS. 4A and 4B. The valve shown in FIGS. 4A and 4B has a shaft 400 and flap 410. Often prior art valves have a "cracking pressure which will increase as the flow threshold increases". The present invention is designed to open at a predetermined flow rate (in this specific application above 5 liters/minute) and keep on opening as the flow rate increases causing the pressure to stay around a certain level as the flow increases. Most umbrella valves will open at a certain pressure and not open any further as the flow rate increases, causing the pressure to increase as the flow increases.

The improvement of the present invention is seen in FIG. 5. Using a simple variable orifice 200 if the flow rate is changed between 5 and 15 liters per minute a dramatic change in PEEP will also occur. The PEEP range for the variable orifice 52 is 13 cmH$_2$O. The best result obtained from prior art umbrella valves 54 was a PEEP range of 4.9 cmH$_2$O. The best result gained from the present invention 56 is a PEEP range of 2.8 cmH$_2$O.

Figure 6:
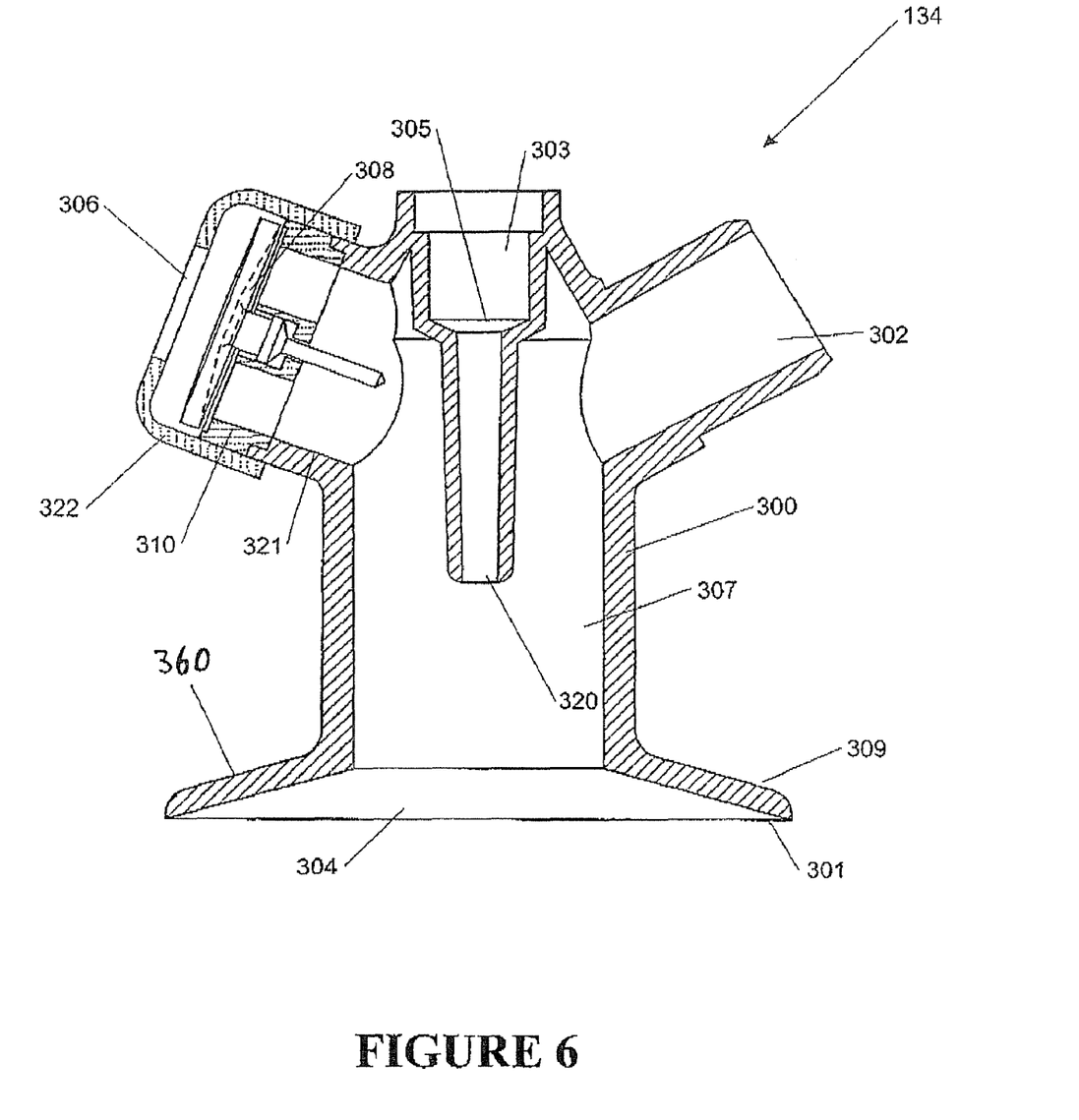
FIG. 6 is a sectional view of the pressure regulator according to a further embodiment of the present invention.
Figure 7:
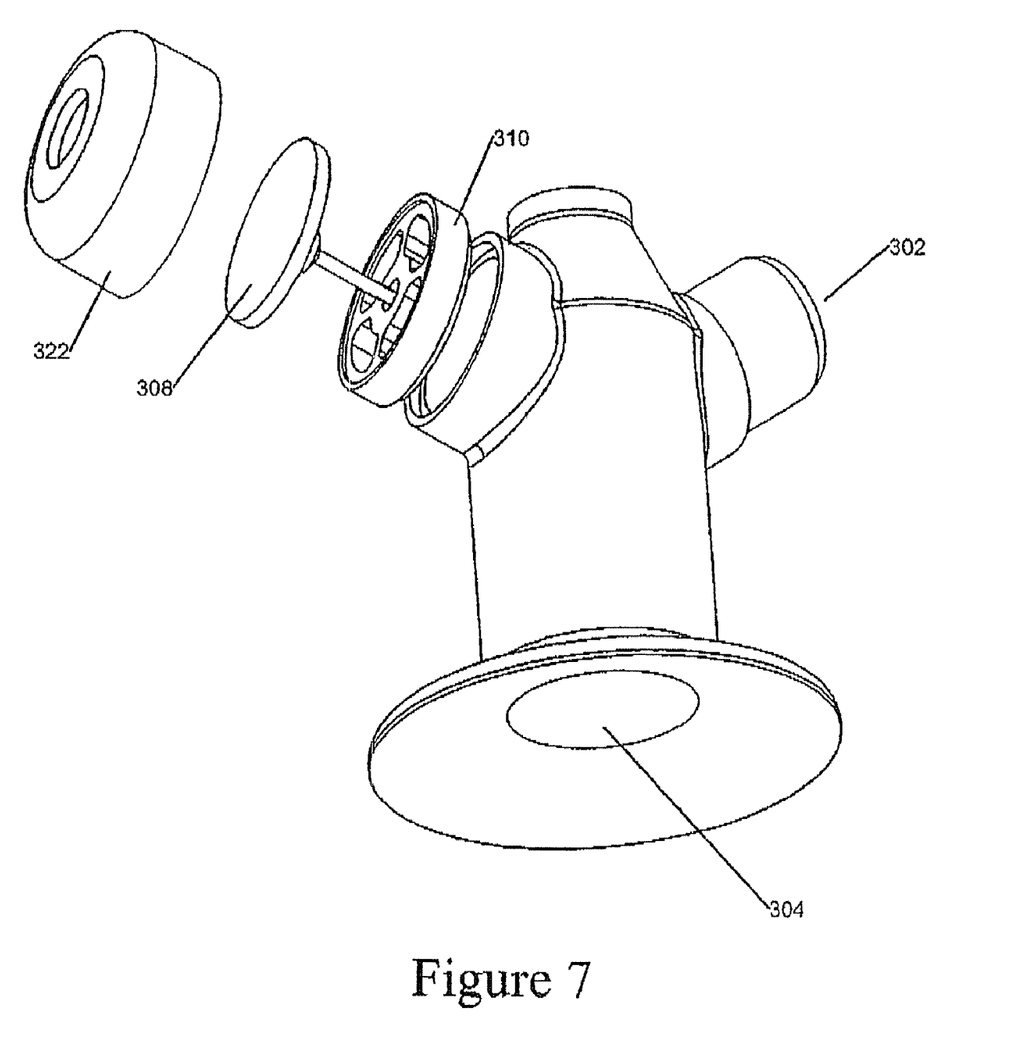
FIG. 7 is a perspective view of the pressure regulator according to a further embodiment of the present invention.

Referring to FIG. 6 we see an alternate embodiment of the pressure regulator 134. Located between the inlet 302 and the orifice 306 is a PEEP valve 308, preferably in the umbrella valve described previously. Also included is an inlet 303 including a duck billed valve 305 which is normally closed, for introducing tubes down the trachea for suctioning, delivery of surfactant etc.

The manifold 300 is shaped to enable ease of use; it is designed to enable one handed operation. The manifold is wide and short and in this embodiment, shown in FIG. 6, it is cylindrical. At the outlet to the neonate 304 connected to the manifold 300 is a flange 301. When used with a mask the flange 301 enables the operator to apply pressure to fluidically seal the mask to the neonate's nose and mouth. The flange 301 also enables an operator to use a digit to occlude orifice 306 to vary pressure between the PIP and PEEP. The operator does this by placing their thumb and middle finger on the flange 301 at 309 and 360 and using their index finger to seal orifice 306. The orifice manifold 321 is at an angle shown at 309 to the manifold 300. This angle allows the index finger to be in a natural position to occlude orifice 306. The alternate embodiment of the pressure regulator 134 operates in the same way as the preferred embodiment described above.

New born neonates often lack surfactant in their lungs. The present invention when used with an endotracheal tube makes it easy to administer surfactant to a patient without the need to remove the breathing assistance apparatus from the patient. By using a syringe or other device known in the art the operator can administer surfactant to the neonate by pushing the end of the syringe through the duck billed valve 305 located opposite the inlet to the neonate 301 and administrating the surfactant to the neonate.

The duck billed valve 305 is normally fluidly sealed but upon insertion of the syringe opens to allow the end of the syringe to enter the interior of the manifold 307. The duck billed valve bills 320 seal around the end of the syringe keeping the manifold 300 sealed. The valve bills 320 are made out of silicone rubber or other suitable material as is known in the art. Because surfactant is a viscous fluid this is advantageous over administering surfactant using multi lumen endotracheal tubes.

The duck billed valve 305 can also be used to suction a neonate to remove airway secretions. Suctioning is performed using a catheter inserted through the duck billed valve down the endotracheal tube. The bills of the valve seal around the inserted catheter thereby maintaining airway pressure. The duck billed valve is retained in a housing in such a way that any instrument inserted into the valve is guided directly into the top of an endotracheal tube (or nasal mask or other interface as are shown in the art), fitted at the outlet to the neonate 304, through the cylindrical tube guide 340.

Figure 8:
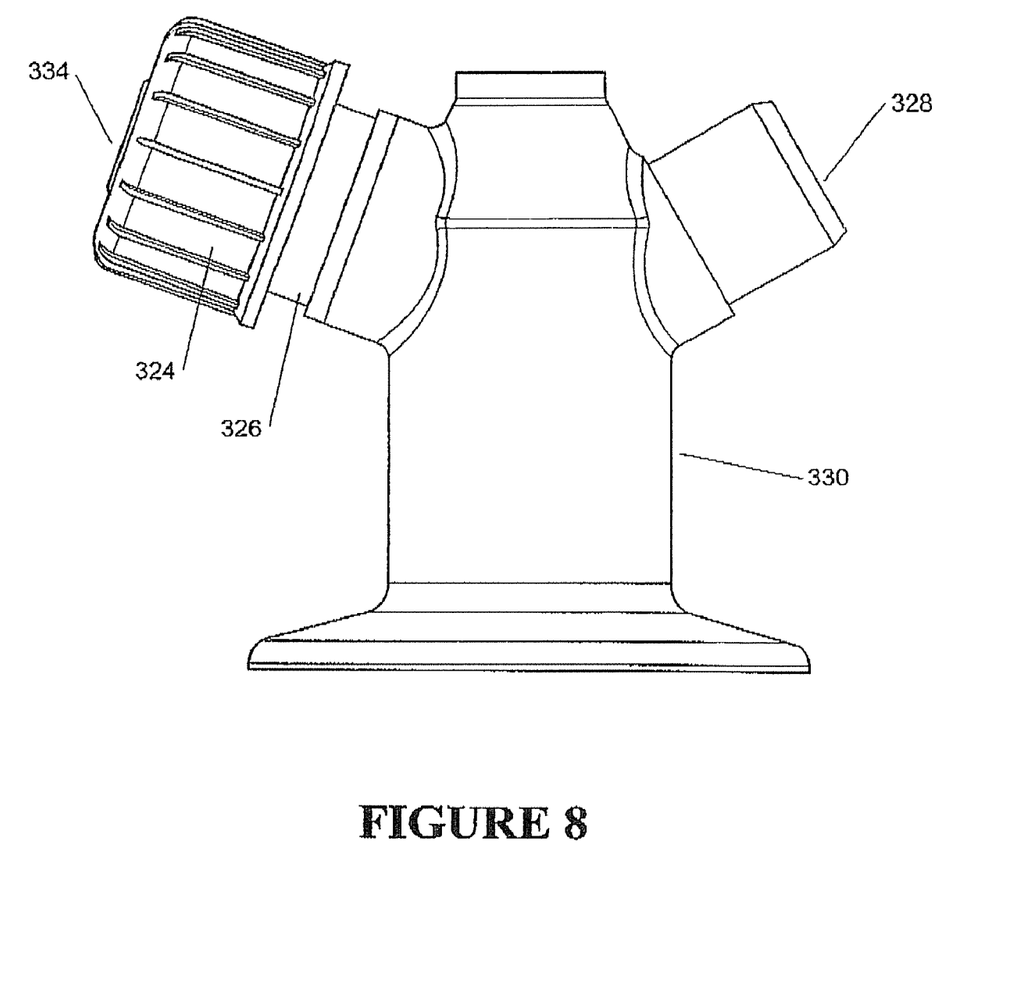
FIG. 8 is a front elevation of the pressure regulator according to a still further embodiment of the present invention.
Figure 9:
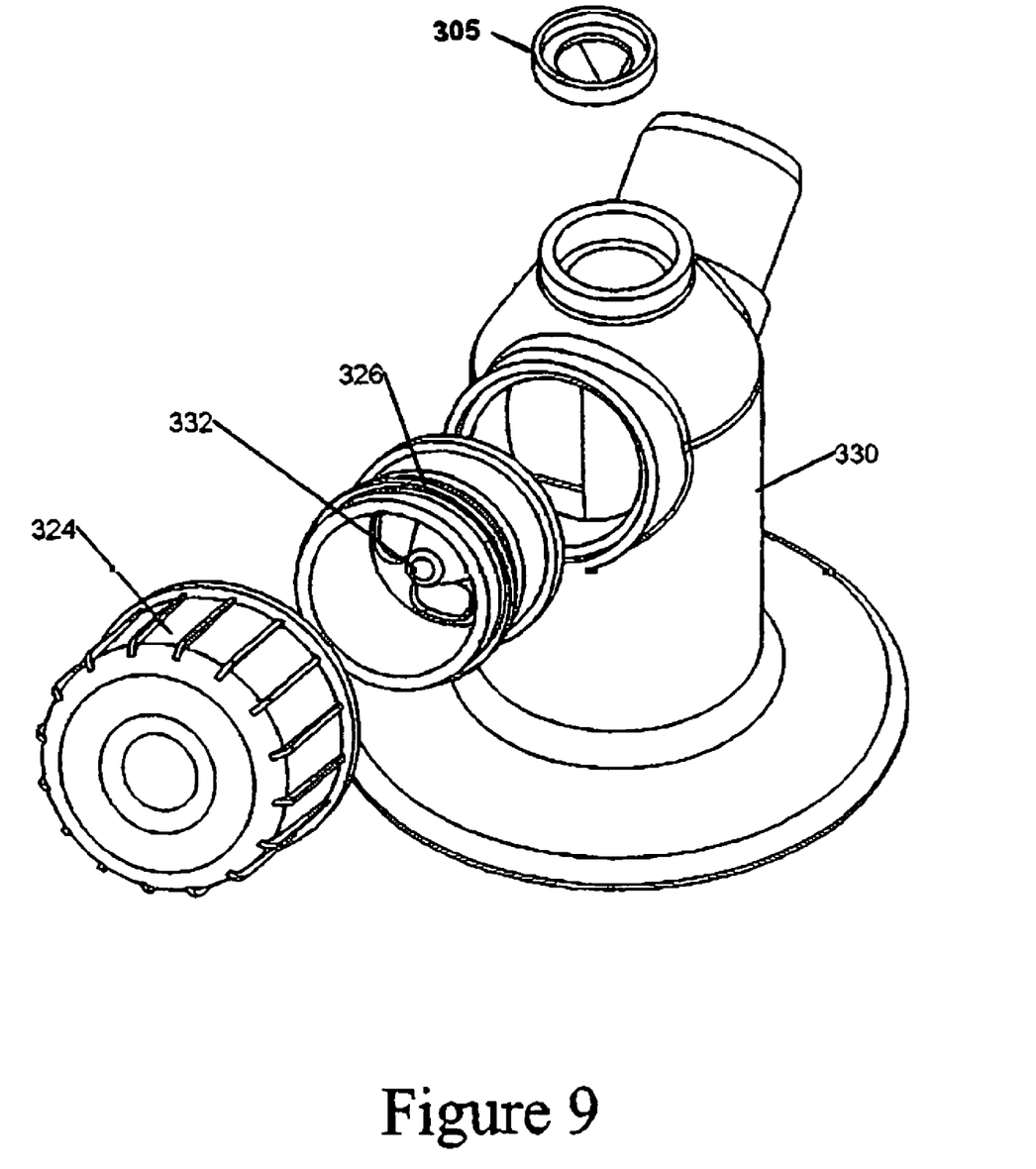
FIG. 9 is a perspective view of the pressure regulator according to a still further embodiment of the present invention.

FIG. 8 and FIG. 9 illustrate an alternate embodiment of the pressure regulator 134. In this case the PEEP is variable as opposed to a set pop-off valve. The delivered gases are varied between the PIP with orifice 334 occluded, and the PEEP with the orifice 334 unoccluded. There is a jet outlet 332 positioned between the inlet 328 and the orifice 334. The flow rate of the gases through the jet outlet 332 is controlled by the proximity of a screw on cap 324. The traveled distance of the screw on cap on the thread 325 determines the restriction to the orifice 332 and therefore varies the PEEP valve. The closer the screw on cap 324 to the jet outlet 332, the smaller the gas flow rate through the orifice 334. The manifold 330 as otherwise described in previous embodiments.

The invention claimed is:

1. A device for use with a breathing assistance apparatus which in use conveys gases to a neonatal infant requiring resuscitation or breathing assistance, comprising:

a housing, having an inlet and a first outlet, said inlet adapted to be in fluid communication with a breathing assistance apparatus and said first outlet adapted to be in fluid communication with said infant, said housing also including an aperture adapted to allow a surfactant delivery tube to be introduced and removed through said aperture, said device adapted so that said delivery tube can deliver surfactant to a patient while said breathing assistance apparatus provides resuscitation breathing assistance, said aperture including a seal adapted to prevent gas flow through said aperture in use, said housing further including a second outlet that is adapted to act as a venting aperture, and a pressure relief valve located in the flow path between said inlet and said second outlet, said second outlet and said housing mutually adapted so that in use a user can hold said housing in position with one hand, and occlude and un-occlude said second outlet with one finger of said one hand to vary the pressure at said first outlet between PIP with said second outlet occluded and all the flow of gases from said inlet passing through said first outlet, and PEEP with said second outlet unoccluded, and a portion of said flow of gases from said inlet passing through said second outlet.

2. A device as claimed in claim 1 wherein said pressure relief valve comprises an elastomeric member having at least two configurations: a first configuration where said elastomeric member blocks the flow path between said inlet and said second outlet, and a second configuration where said elastomeric member allows a portion of the flow of gases from said inlet to flow through said second outlet, said elastomeric member adapted to switch from said first configuration to said second configuration at a predetermined flow rate.

3. A device as claimed in claim 2 wherein said seal is formed as a duck billed valve, opening into said housing.

4. A device as claimed in claim 3 wherein said aperture and said first outlet are arranged substantially coaxially.

5. A device as claimed in claim 1 wherein said pressure relief valve comprises a screw-on cap located over said second outlet, said housing including a thread to allow location and adjustment of said screw-on cap, and wherein said second outlet is formed as a jet outlet, the flow rate of the gases through said jet outlet varied by adjusting the position of said cap by rotating said cap on said thread, and wherein the closer the screw-on cap is to said jet outlet, the smaller the gas flow rate through said jet outlet.

6. A device as claimed in claim 5 wherein said seal is formed as a duck billed valve, opening into said housing.

7. A device as claimed in claim 6 wherein said aperture and said first outlet are arranged substantially coaxially.

* * * * *